United States Patent
Fuller et al.

(10) Patent No.: US 8,735,021 B2
(45) Date of Patent: *May 27, 2014

(54) COBALT(II) TETRAMETHOXYPHENYLPORPHYRIN (COTMPP) IONOMER STABILIZATION TO PREVENT ELECTRODE DEGRADATION

(75) Inventors: Timothy J. Fuller, Pittsford, NY (US); Michael R. Schoeneweiss, West Henrietta, NY (US); Junliang Zhang, Rochester, NY (US)

(73) Assignee: GM Global Technology Operations LLC, Detroit, MI (US)

( * ) Notice: Subject to any disclaimer, the term of this patent is extended or adjusted under 35 U.S.C. 154(b) by 494 days.

This patent is subject to a terminal disclaimer.

(21) Appl. No.: 12/761,501

(22) Filed: Apr. 16, 2010

(65) Prior Publication Data

US 2011/0256467 A1    Oct. 20, 2011

(51) Int. Cl.
    *H01M 8/10*        (2006.01)

(52) U.S. Cl.
    USPC ............ 429/492; 429/491; 429/483; 429/479

(58) Field of Classification Search
    USPC .................................. 429/492, 491, 482, 479
    See application file for complete search history.

(56) References Cited

U.S. PATENT DOCUMENTS

| | | | |
|---|---|---|---|
| 5,006,408 A | 4/1991 | Green et al. | |
| 5,021,602 A | 6/1991 | Clement et al. | |
| 5,037,917 A | 8/1991 | Babb et al. | |
| 5,066,746 A | 11/1991 | Clement et al. | |
| 5,159,037 A | 10/1992 | Clement et al. | |
| 5,159,038 A | 10/1992 | Babb et al. | |
| 5,910,378 A | 6/1999 | Debe et al. | |
| 6,124,060 A | 9/2000 | Akita et al. | |
| 6,183,668 B1 | 2/2001 | Debe et al. | |
| 6,277,512 B1 | 8/2001 | Hamrock et al. | |
| 6,444,343 B1 | 9/2002 | Prakash et al. | |
| 6,523,699 B1 | 2/2003 | Akita et al. | |
| 6,559,237 B1 | 5/2003 | Mao et al. | |
| 6,847,518 B2 | 1/2005 | Fukuda et al. | |
| 6,875,537 B2 | 4/2005 | Tani et al. | |
| 6,926,984 B2 | 8/2005 | Asano et al. | |
| 6,933,068 B2 | 8/2005 | Asano et al. | |
| 6,953,653 B2 | 10/2005 | Smith et al. | |
| 6,986,962 B2 | 1/2006 | Oyanagi et al. | |
| 7,001,929 B2 | 2/2006 | Goto et al. | |

(Continued)

FOREIGN PATENT DOCUMENTS

| | | |
|---|---|---|
| CN | 1902777 A | 1/2007 |
| CN | 102005586 A | 4/2011 |

(Continued)

OTHER PUBLICATIONS

Smith, D.W. et al., "Perfluorocyclobutane Aromatic Polyethers. Synthesis and Characterization of New Siloxane-Containing Fluoropolymers," Macromolecules 1996, v. 29, pp. 852-860.

(Continued)

*Primary Examiner* — Laura Weiner

(74) *Attorney, Agent, or Firm* — Brooks Kushman P.C.

(57) ABSTRACT

A membrane/electrode assembly for fuel cell applications includes an ion conducting polymer and a porphyrin-containing compound at least partially dispersed within the ion conducting polymer, a first electrode and a second electrode. At least one of the first and second electrodes also includes the porphyrin-containing compound. The membrane/electrode assembly exhibits improved performance over membrane/electrode assembly not incorporating such porphyrin-containing compounds.

4 Claims, 5 Drawing Sheets

(56) References Cited

U.S. PATENT DOCUMENTS

| | | |
|---|---|---|
| 7,045,241 B2 | 5/2006 | Akita et al. |
| 2001/0018144 A1 | 8/2001 | Watakabe et al. |
| 2002/0014405 A1 | 2/2002 | Arcella et al. |
| 2003/0017379 A1 | 1/2003 | Menashi |
| 2004/0214058 A1 | 10/2004 | Tada et al. |
| 2004/0214065 A1 | 10/2004 | Kanaoka et al. |
| 2005/0014927 A1 | 1/2005 | Akita |
| 2005/0043487 A1 | 2/2005 | Felix et al. |
| 2005/0048342 A1 | 3/2005 | Wakahoi et al. |
| 2005/0053810 A1 | 3/2005 | Kato et al. |
| 2005/0058864 A1 | 3/2005 | Goebel |
| 2005/0064260 A1 | 3/2005 | Otsuki et al. |
| 2005/0100770 A1 | 5/2005 | Sugawara et al. |
| 2005/0106440 A1 | 5/2005 | Komiya |
| 2005/0116206 A1 | 6/2005 | Kakuta et al. |
| 2005/0130024 A1 | 6/2005 | Otsuki et al. |
| 2005/0142397 A1 | 6/2005 | Wakahoi et al. |
| 2005/0143530 A1 | 6/2005 | Iwadate et al. |
| 2005/0175886 A1 | 8/2005 | Fukuda et al. |
| 2005/0197467 A1 | 9/2005 | Komiya et al. |
| 2005/0227138 A1 | 10/2005 | Fukuda et al. |
| 2005/0233181 A1 | 10/2005 | Wariishi et al. |
| 2005/0260474 A1 | 11/2005 | Asano et al. |
| 2006/0019147 A1 | 1/2006 | Fukuda et al. |
| 2006/0127728 A1 | 6/2006 | Otsuki et al. |
| 2006/0177719 A1 | 8/2006 | Fuller et al. |
| 2007/0042242 A1 | 2/2007 | Tada et al. |
| 2007/0099054 A1 | 5/2007 | Fuller et al. |
| 2007/0141237 A1 | 6/2007 | Okiyama et al. |
| 2008/0027152 A1 | 1/2008 | Maier et al. |
| 2009/0278083 A1 | 11/2009 | Fuller et al. |
| 2009/0278091 A1 | 11/2009 | MacKinnon et al. |
| 2009/0281245 A1 | 11/2009 | MacKinnon et al. |
| 2009/0281262 A1 | 11/2009 | MacKinnon et al. |
| 2009/0281270 A1 | 11/2009 | Fuller et al. |

FOREIGN PATENT DOCUMENTS

| | | |
|---|---|---|
| JP | 2003535929 t | 12/2003 |
| JP | 2005105176 A | 4/2005 |
| JP | 2005129298 A | 5/2005 |
| JP | 2005166557 A | 6/2005 |
| JP | 2005179380 A | 7/2005 |
| JP | 2009 249 487 A | 10/2009 |
| WO | 2004/051776 | 6/2004 |
| WO | 2005/060039 A1 | 6/2005 |
| WO | 2007/052954 A1 | 5/2007 |

OTHER PUBLICATIONS

Smith, D.W. et al., "Perfluorocyclobutane (PFCB) polyaryl ethers: versatile coatings material," J. of Fluorine Chem., v. 104, pp. 109-117 (2000).

Souzy, R. et al., "Functional fluoropolymers for fuel cell membranes," Solid State Ionics, v. 176, pp. 2839-2848 (2005).

Souzy, R. et al., "Functional fluoropolymers for fuel cell membranes," Prog. Polm. Sci. 30, 2005, pp. 644-687.

"Fluorel Technical Data Sheets," MatWeb Material Property Data website, http://www.matweb.com/search/GetMatIsByTradename.aspx?navletter=F&tn=Fluorel%E2%84%A2.

Nafion perfluorinated resin, Sigma-Aldrich Online Catalog, http://www.sigmaaldrich.com/catalog/ProductDetail.do?lang=en&N4=495786|ALDRICH&N5=SEARCH_CONCAT_PNO|BRAND_KEY&F=SPEC.

Ford, L.A. et al., "New Aromatic Perfluorovinyl Ether Monomers Containing the Sulfonimide Acid Functionality," Polymeric Materials Science & Eng., v. 83, 2000, pp. 10-11 (American Chemical Society).

Souzy, R. et al., "Synthesis and (co)polymerization of monofluoro, difluoro, trifluorostyrene and ((trifluorovinyl)oxy) benzene," Prog. Polm. Sci. 29 (2004), pp. 75-106.

COBALT(II) TETRAMETHOXYPHENYLPORPHYRIN (COTMPP) IONOMER STABILIZATION TO PREVENT ELECTRODE DEGRADATION

TECHNICAL FIELD

The present invention relates to ion conducting membranes and electrodes for fuel cell applications.

BACKGROUND

Fuel cells are used as an electrical power source in many applications. In particular, fuel cells are proposed for use in automobiles to replace internal combustion engines. A commonly used fuel cell design uses a solid polymer electrolyte ("SPE") membrane or proton exchange membrane ("PEM") to provide ion transport between the anode and cathode.

In proton exchange membrane type fuel cells, hydrogen is supplied to the anode as fuel and oxygen is supplied to the cathode as the oxidant. The oxygen can either be in pure form ($O_2$) or air (a mixture of $O_2$ and $N_2$). PEM fuel cells typically have a membrane electrode assembly ("MEA") in which a solid polymer membrane has an anode catalyst on one face, and a cathode catalyst on the opposite face. The anode and cathode layers of a typical PEM fuel cell are formed with porous conductive materials, such as woven graphite, graphitized sheets, or carbon paper to enable the fuel to disperse over the surface of the membrane facing the fuel supply electrode. Each electrode has finely divided catalyst particles (for example, platinum particles), supported on carbon particles, to promote oxidation of hydrogen at the anode and reduction of oxygen at the cathode. Protons flow from the anode through the ion conductive polymer membrane to the cathode where they combine with oxygen to form water which is discharged from the cell. Typically, the ion conductive polymer membrane includes a perfluorinated sulfonic acid ("PFSA") ionomer.

The MEA is sandwiched between a pair of porous gas diffusion layers ("GDL"), which in turn are sandwiched between a pair of non-porous, electrically conductive elements or plates. The plates function as current collectors for the anode and the cathode, and contain appropriate channels and openings formed therein for distributing the fuel cell's gaseous reactants over the surface of respective anode and cathode catalysts. In order to produce electricity efficiently, the polymer electrolyte membrane of a PEM fuel cell must be thin, chemically stable, proton transmissive, non-electrically conductive and gas impermeable. In typical applications, fuel cells are provided in arrays of many individual fuel cell stacks in order to provide high levels of electrical power.

One mechanism by which ion conducting polymer membranes degrade is via loss of fluorine (i.e., fluoride emission) under open circuit voltage ("OCV") and dry operating conditions at elevated temperatures. Additives to PFSA membranes are required to improve fuel cell life, increase membrane durability and reduce fluoride emissions under these conditions.

Accordingly, there is a need for improved ion conducting membranes with reduced fluoride emissions.

SUMMARY OF EXEMPLARY EMBODIMENTS OF THE INVENTION

The present invention solves one or more problems of the prior art by providing in at least one embodiment an ion conducting membrane/electrode combination for fuel cell applications. The ion conducting membrane/electrode assembly includes an ion conducting membrane, a first electrode, and a second electrode. The first electrode is disposed over a first side of the ion conducting membrane while the second electrode is disposed over a second side of the ion conducting membrane. The ion conducting membrane includes an ion conducting polymer and a porphyrin-containing compound at least partially dispersed within the ion conducting polymer in a sufficient amount to reduce fluoride emissions from the membrane. Similarly, the one or both of the first and second electrodes includes an ion conducting polymer and a porphyrin-containing compound at least partially dispersed within the ion conducting polymer in a sufficient amount to reduce fluoride emissions from the membrane. Moreover, the incorporation of a porphyrin-containing compound advantageously increases membrane and electrode life while decreasing electrode voltage degradation in fuel cells operating at open circuit conditions at 95° C. and 50% relative humidity.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies *mutatis mutandis* to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 1:
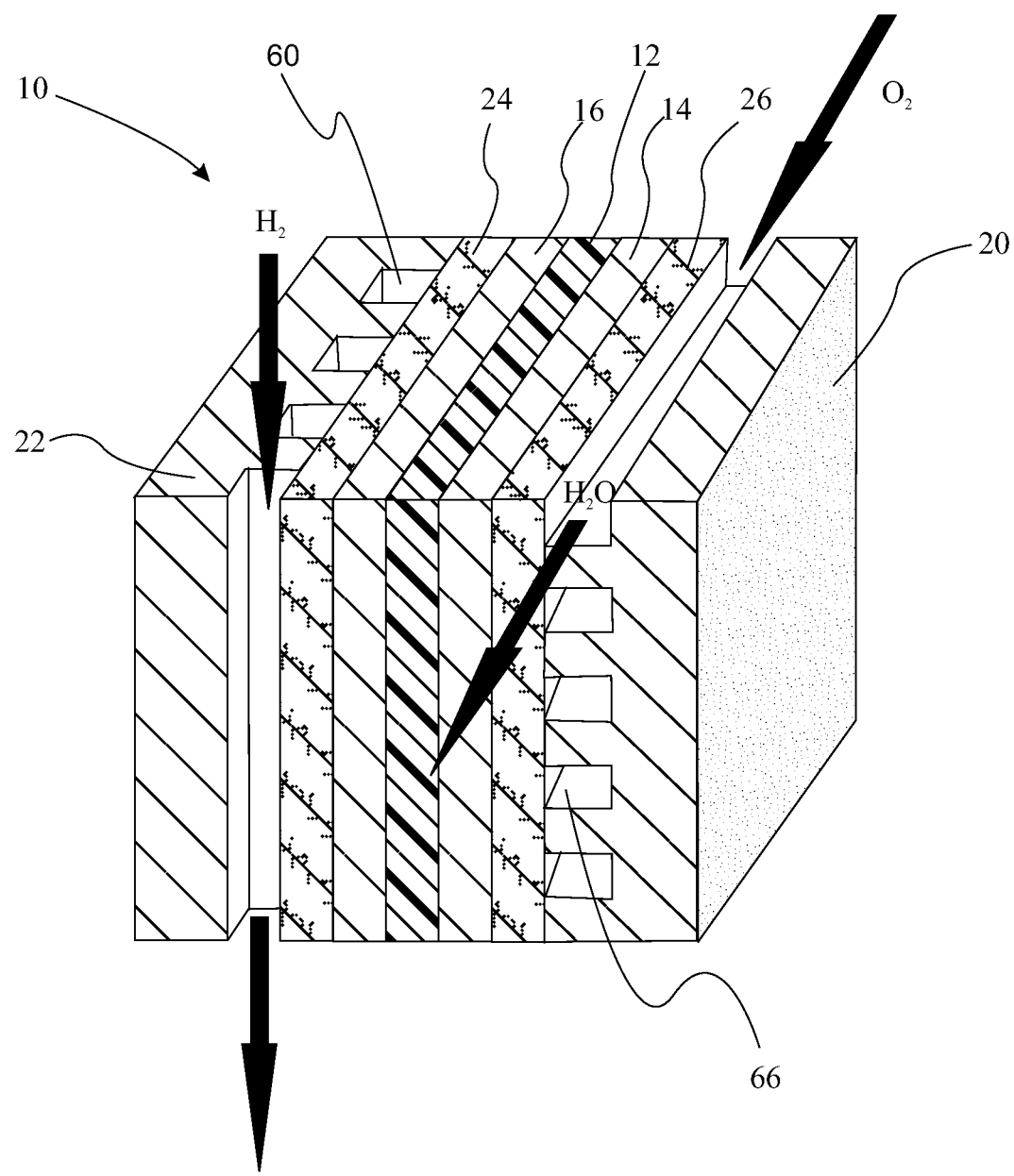
FIG. 1 is a schematic illustration of a fuel cell that incorporates an ion conducting membrane of one or more embodiments of the invention.

With reference to FIG. 1, a fuel cell that incorporates an ion conducting membrane of one or more embodiments of the invention is provided. PEM fuel cell 10 includes polymeric ion conductive membrane 12 disposed between cathode catalyst layer 14 (the first electrode) and anode catalyst layer 16 (the second electrode). Cathode catalyst layer 14 and anode catalyst layer 16 are electrode layers. Polymeric ion conductive membrane 12 and at least one of cathode catalyst layer 14 and anode catalyst layer 16 include an effective amount of porphyrin-containing compound as set forth below. Fuel cell 10 also includes conductive plates 20, 22, gas channels 60 and 66, and gas diffusion layers 24 and 26.

In an embodiment of the present invention, an ion conducting membrane and one or both of a first and a second electrode for fuel cell applications include an ion conducting polymer and a porphyrin-containing compound at least partially dispersed within the ion conducting polymer. In a variation, the porphyrin-containing compound includes a moiety having formula 1:

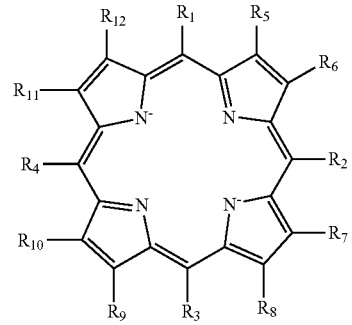

wherein:
$R_1$, $R_2$, $R_3$, $R_4$, $R_5$, $R_6$, $R_7$, $R_8$, $R_9$, $R_{10}$, $R_{11}$, $R_{12}$ are each independently hydrogen, alkyl, or aryl. In a refinement, $R_1$, $R_2$, $R_3$, $R_4$, are each independently substituted or unsubstituted alkyl or phenyl. In another refinement, $R_1$, $R_2$, $R_3$, $R_4$, are each phenylmethoxy. In still another refinement, $R_5$, $R_6$, $R_7$, $R_8$, $R_9$, $R_{10}$, $R_{11}$, $R_{12}$ are each hydrogen. In this context, substitutions may be with halogens, methoxy, ethoxy, and the like. In addition, in the case of aryl and phenyl, substitutions may also be with alkyl groups.

In another variation of the present embodiment, the porphyrin-containing compound is present in an amount from about 0.001 to about 50 weight percent of the total weight of the ion conducting membrane. In a refinement, the porphyrin-containing compound is present in an amount from about 0.1 to about 10 weight percent of the total weight of the ion conducting membrane.

In still another variation of the present embodiment, the porphyrin-containing compound has formula 2:

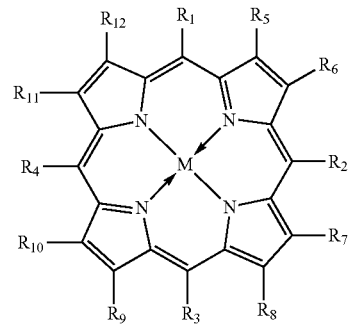

wherein M is a metal or metal-containing moiety. Examples of suitable metals for M or for inclusion in the metal containing moiety include Co, Fe, Mg, Mn, Cu, Ni, Pd, Ru, Vn, Zn, Al, B, Si, Al, In, Pb, Ag, Sn, Ti, V, Pt, Ce, and the like. Specific examples for M include $Co^{2+}$, $Co^{3+}$, $Fe^{2+}$, $Fe^{3+}$, $Mg^{1+}$, $Mg^{2+}$, $Mn^{1+}$, $Mn^{2+}$, $Mn^{3+}$, $ClMn^{3+}$, $HOMn^{3+}$, $Cu^{+1}$, $Cu^{2+}$, $Ni^{1+}$, $Ni^{2+}$, $Pd^{1+}$, $Pd^{2+}$, $Ru^{1+}$, $Ru^{2+}$, $Ru^{4+}$, $Vn^{4+}$, $Zn^{1+}$, $Zn^{2+}$, $Al^{3+}$, B, $Si(OH)_2^{2+}$, $Al^{3+}$, $HOIn^{3+}$, $HOIn^{3+}$, $Pb^{2+}$, $Ag^+$, $Sn^{2+}$, $Sn^{4+}$, $Ti^{3+}$, $Ti^{4+}$, $VO^+$, $Pt^{2+}$, $Ce^{3+}$, $Ce^{4+}$.

In another variation of the present embodiment, the ion-conducting membrane and/or one or both of the first and second electrodes further comprise a metal-containing compound having a metal (i.e., metal ion) selected from the group consisting of Ce(III), Ce(IV), Mn(II) and Mn(IV). Examples of metal-containing compounds include $MnO_2$, $Mn_2O_3$, $MnCl_2$, $MnSO_4$, $CeCl_3$, $Ce_2(CO_3)_3$, $CeF_3$, $Ce_2O_3$, $CeO_2$, $Ce(SO_4)_2)$ $Ce(OSO_2CF_3)_3$, and combinations thereof. In a further refinement, the metal-containing compound is selected from the group consisting of $MnO_2$, $Mn_2O_3$ $MnCl_2$, $MnSO_4$, and combinations thereof.

As set forth above, the membrane of the present invention includes an ion conducting polymer. Such polymers include sulfonated tetrafluoroethylene-based fluoropolymer-copolymers. Sometimes this class of polymers is referred to as perfluorosulfonic acid (PFSA) polymers. Specific examples of such polymers include the Nafion® line of polymers commercially available from E.I. du Pont de Nemours and Company. In another refinement, the ion conducting polymer comprises a perfluorocyclobutyl moiety. Examples of these suitable polymers are set forth in U.S. Pat. Nos. 3,282,875; 3,041,317; 3,718,627; 2,393,967; 2,559,752; 2,593,583; 3,770,567; 2,251,660; U.S. Pat. Pub. No. 2007-0099054; U.S. patent application Ser. Nos. 12/197,530 filed Aug. 25, 2008; 12/197,537 filed Aug. 25, 2008; 12/197,545 filed Aug. 25, 2008; and 12/197,704 filed Aug. 25, 2008; the entire disclosures of which are hereby incorporated by reference.

An example of a block copolymer having perfluorocyclobutyl moieties includes polymer segments 1 and 2:

 [1]

 [2]

connected by a linking group $L_1$ to form polymer units 3 and 4:

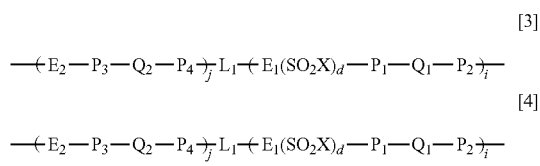

[3]

[4]

wherein:
$Z_1$ is a protogenic group such as $-SO_2X$, $-PO_3H_2$, $-COX$, and the like;
$E_1$ is an aromatic-containing moiety;
$E_2$ is an unsulfonated aromatic-containing and/or aliphatic-containing moiety;
$L_1$ is a linking group;
X is an —OH, a halogen, an ester, or

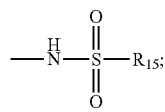

$d$ is a number of $Z_1$ functional groups attached to $E_1$;
$P_1$, $P_2$, $P_3$, $P_4$ are each independently absent, —O—, —S—, —SO—, —SO$_2$—, —CO—, —NH—, NR$_{13}$—, —R$_{14}$—, and
$R_{11}$ is $C_{1-25}$ alkyl, $C_{1-25}$ aryl or $C_{1-25}$ arylene;
$R_{14}$ is $C_{1-25}$ alkylene, $C_{1-25}$ perfluoroalkylene, or $C_{1-25}$ arylene;
$R_{15}$ is trifluoromethyl, $C_{1-25}$ alkyl, $C_{1-25}$ perfluoroalkylene, $C_{1-25}$ aryl, or another $E_1$ group;
$Q_1$, $Q_2$ are each independently a fluorinated cyclobutyl moiety;
i is a number representing the repetition of polymer segment 1; and,
j is a number representing the repetition of a polymer segment 2.

In a variation of the present embodiment, polymer segment 1 is formed by sulfonating the following polymer segment:

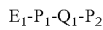

In another variation of the present invention, $Q_1$, $Q_2$ are perfluorocyclobutyl moieties. Examples of perfluorocyclobutyl moieties may include, but are not limited to, formulas 5 or 6

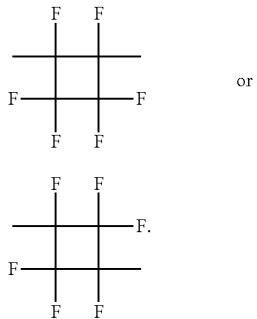

[5]

or

[6]

Formulae 7 and 8 provides more specific examples of polymer units 3 and 4:

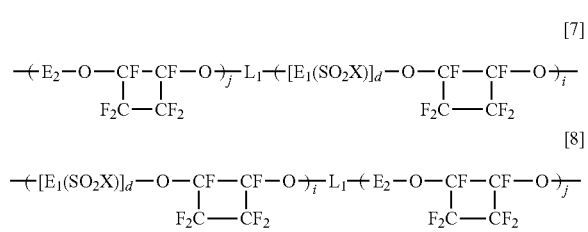

[7]

[8]

In a variation of the present embodiment, polymer segments 3 and/or 4 may be repeated to form:

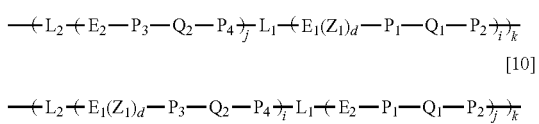

[9]

[10]

where $L_2$ is absent or a linking group and k is an integer representing the repetition of the polymer units 3 or 4.

In another variation of the present invention, $L_1$ and $L_2$ each independently comprise an ether, imide, amide, ester, amine, ketone or acyl groups. Examples of $L_1$ and $L_2$ may include, but are not limited to, the following linking groups

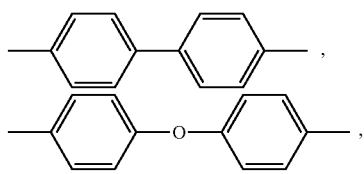

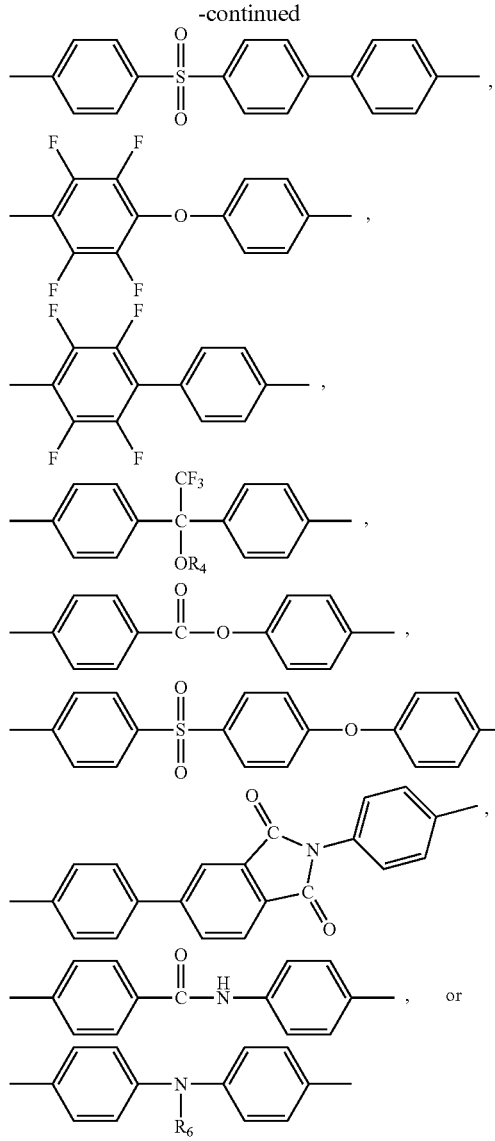

where $R_5$ is an organic group, such as an alkyl or acyl group.

In another variation of the present embodiment, $E_1$ and $E_2$ include one or more aromatic rings. For example, $E_1$ and $E_2$, include one or more of phenyl, biphenyl, terphenyl, naphthalenyl, phenanthrenyl, diphenyl ether, 9,9'-diphenylfluorene, diphenylsulfide, diphenylcyclohexyl methane, diphenyldimethylsilane, α-methylstilbene, hydroquinone diphenyl ether, sulfonated phenyl, α-methylstilbene, diphenylcyclohexyl methane or bisphenol A. In a perfluorocyclobutane block copolymer, $E_1$ is typically different from $E_2$. In one further refinement, $E_1$ is a sulfonatable aromatic moiety while $E_2$ is not.

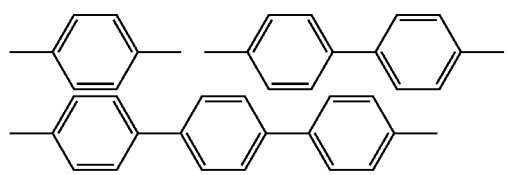

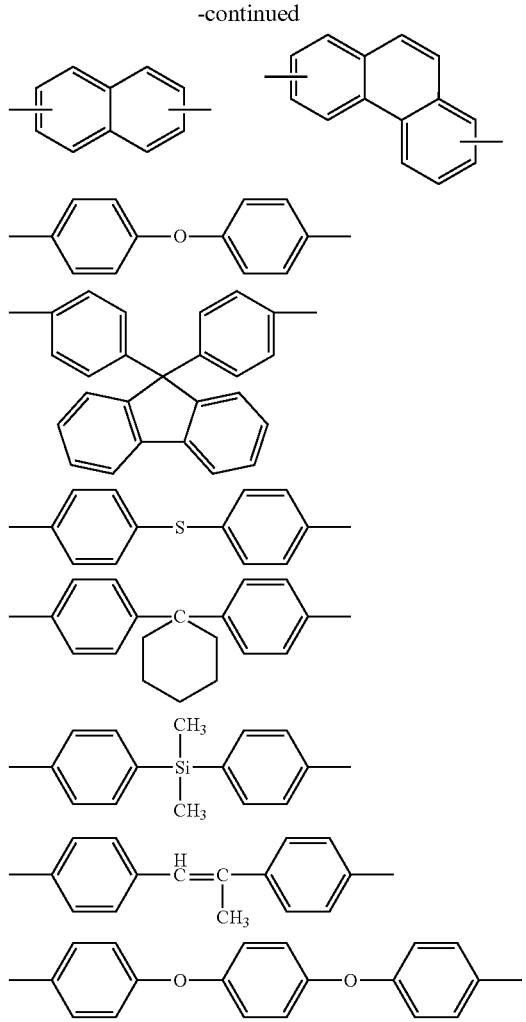

In refinement of the present embodiment, the combination of $E_1$ and $E_2$ are chosen such that $E_1$ can be selectively sulfonated without affecting $E_2$ in an oligomer or a polymer comprising both $E_1$ and $E_2$. Examples of $E_2$ useful in this refinement include, but are not limited to, one or more of the following functional groups, diphenyl sulfone, triphenylphosphate, 2,2'-diphenyl hexafluoropropane, and diphenylketone:

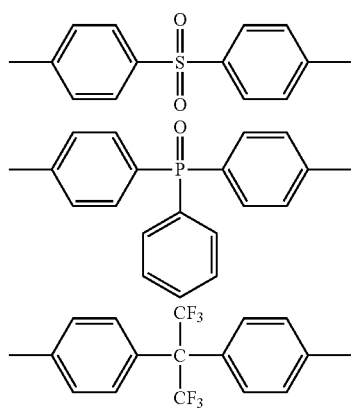

-continued

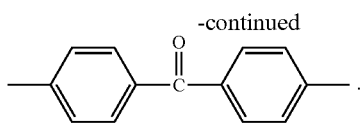

The following examples illustrate the various embodiments of the present invention. Those skilled in the art will recognize many variations that are within the spirit of the present invention and scope of the claims.

Membrane Preparation. To a 20 wt. % solids dispersion of DE2020 Nafion® solution (DuPont de Nemours) is added Cobalt(II)tetramethoxyphenylporphyrin (CoTMPP) at 5 wt. % based on perfluorosulfonic acid (PFSA) polymer solids in 1-propanol and water (3/2 weight ratio) and the mixture is homogenized with an IKA homogenizer for about 4 minutes. The CoTMPP is soluble in the ionomer solution, which is centrifuged to remove suspended air bubbles. The blood-red supernate is coated on glass with an 8-mil coating gap, Bird applicator, and the resultant wet film is then heated at 80° C. for 1 h in air and then at 140° C. for 4 h under vacuum. The green film is floated off glass and air-dried to obtain a 16-μm membrane.

Electrode Preparation. Cobalt(II)tetramethoxyphenylporphyrin (CoTMPP) is added at 5 wt. % and 10 wt. % based on the solid ionomer content into the electrode coating ink. The ink contains $Pt_3Co$/Vulcan (TKK, Pt 29 wt. %) catalyst, DE2020 (Dupont) ionomer and solvent. The solvent consists of ethanol, water and isopropanol at a volume ratio of 2:2:1. The ionomer/carbon ratio is 0.95, and the carbon content in the ink is 5 wt. %. The ink is homogenized by ball-milling for 3 days before coating on a decal substrate (expanded polytetrafluoroethylene). The electrode is prepared with a typical decal-transfer and hot-press procedure that is well known to those skilled in the art.

CoTMPP (at 5 and 10 wt. %) is added to (1) electrodes and membranes, (2) electrodes only, and (3) membrane only. A comparison is made to (4) a control with no CoTMPP added to either membrane or electrodes. Nafion DE2020 (1000 eq wt) is the ionomer used. The membranes are cycled between 1 V and 0.6 V for nominally 10,000 cycles (5 days of testing) and 30,000 cycles (3 weeks) if no Pt line is observed after 10,000 cycles. A Pt line that forms from Pt catalyst dissolution suggests loss of electrode catalyst. The electrode ionomer is stabilized by adding CoTMPP (and the like) to the electrode or to the electrode and to the membrane. Membranes are submitted for SEM-EDX analysis, and the results are summarized in Table 1. There is no initial performance hit from CoTMPP in the membrane. After 10,000 and 30,000 cycles, fuel cell performance decreases, but this is expected because there was no rejuvenation of the catalyst. None of the CoTMPP membrane electrode assemblies show evidence of membrane or electrode thinning (like the baseline without CoTMPP, which shows both a Pt line and membrane thinning [chemical degradation of the ionomer] and electrode thinning [Pt dissolution and chemical degradation of the ionomer in the electrode]). These results indicate that the CoTMPP stabilizes ionomer in both the membrane and in the electrodes.

TABLE 1

Nafion ® DE2020 Membrane Electrode Assemblies Made with and Without CoTMPP in the Electrodes and Membranes that Were Cycled between 1 Volt and 0.6 Volts and then Cross-Sectioned and Micro-Graphed

| Sample | Electrodes $Pt_3Co$/Vulcan | Membrane (Nafion ® DE2020) | Cycles between 1 V and 0.6 V | Observation |
|---|---|---|---|---|
| 1 | 10% CoTMPP | 10% CoTMPP | 30,000 | No Pt line |
| 2a | 10% CoTMPP | No CoTMPP | 10,000 | Pt line |
| 2b | 10% CoTMPP | No CoTMPP | 20,000 | Pt line |
| 3a | No CoTMPP | 5% CoTMPP | 10,000 | No Pt line |
| 3b | No CoTMPP | 5% CoTMPP | 30,000 | Pt line-cathode inlet only |
| 4 | No CoTMPP | No CoTMPP | 10,000 | Pt line |

Figure 2:
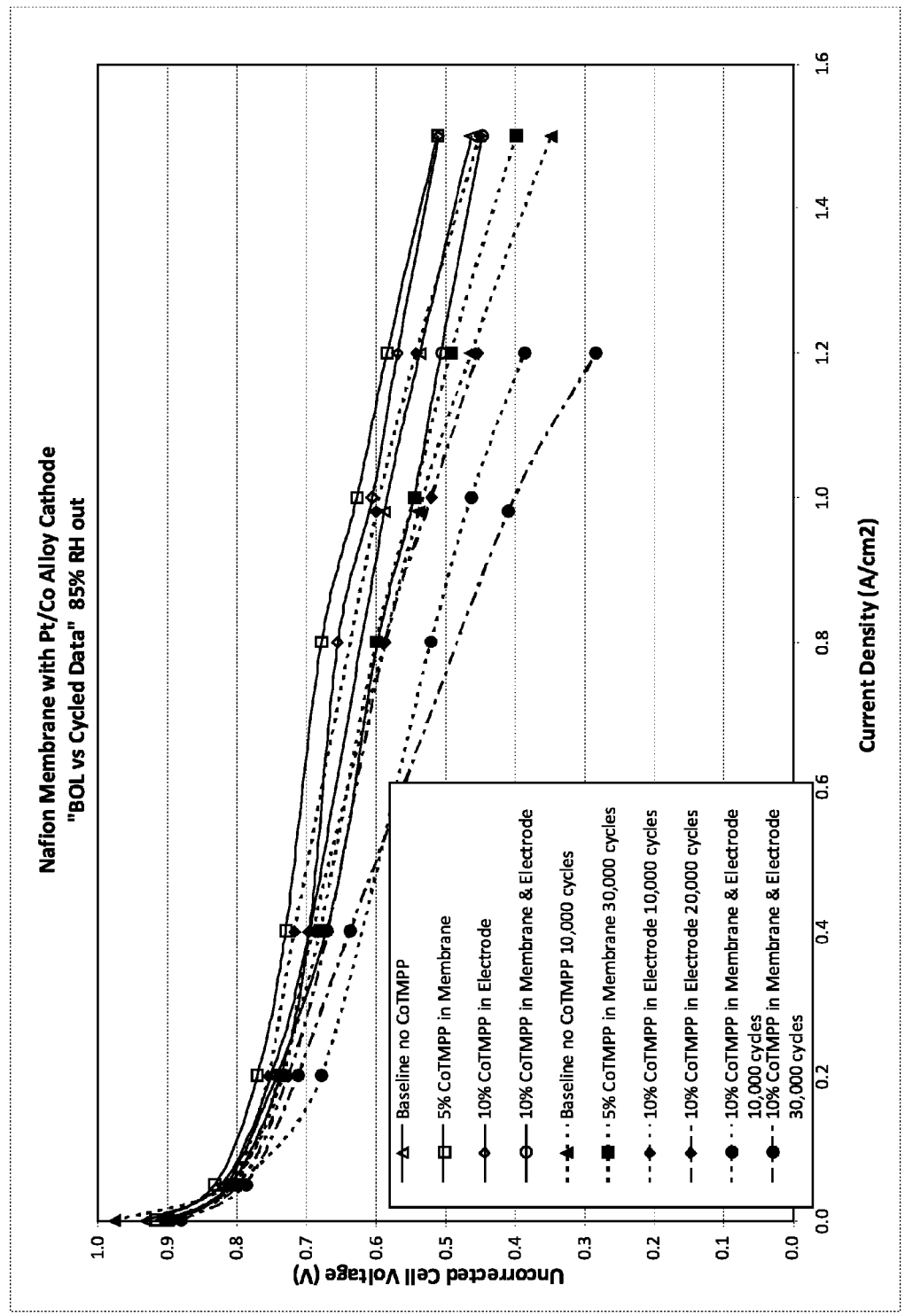
FIG. 2 is a plot of fuel cell performance (cell voltage versus current density, $A/cm^2$) at beginning of life and after cycling between 1 and 0.6 volts at 85% relative humidity exiting the cell for DE2020 Nafion® membranes and electrodes with and without cobalt(II) tetramethoxyphenylporphyrin (CoTMPP).

Performance with voltage cycling of the membranes is shown in FIG. 2. There is no initial performance hit from CoTMPP in the membrane. After 10,000 and 30,000 cycles, fuel cell performance decreases, but there is no rejuvenation of the catalyst. Performance with voltage cycling of the membranes with alloy Pt/Co catalyst is shown in FIG. 2. Performance and the absence of a Pt line in the membrane with CoTMPP in both electrode and the membrane is used as evidence that the ionomer and the Pt in the catalyst layer are stabilized by CoTMPP in both the electrode and the membrane. FIG. 2 is a plot of the fuel cell performance (cell voltage versus current density, $A/cm^2$) at the beginning of life and after cycling between 1 and 0.6 volts at 85% relative humidity exiting the cell for DE2020 Nafion® membranes and electrodes with and without cobalt(II) tetramethoxyphenylporphyrin (CoTMPP). For compositions refer to Table 1: Sample 1 (10% CoTMPP in membrane and in the electrode at beginning of life [Sample 1] and after 10,000 cycles [Sample 1a] and 30,000 cycles [Sample 1b]); Sample 2 (10% CoTMPP in the electrode at beginning of life [Sample 2] and after 10,000 cycles [Sample 2a] and 30,000 cycles [Sample 2b]); Sample 3 (5% CoTMPP in the membrane at beginning of life [Sample 3] and after 30,000 cycles [Sample 3b]); and Sample 4 (baseline material with no CoTMPP at beginning of life). There is a performance loss with increased voltage cycling. For example, Sample 1 lost 130 mV after 10,000 voltage cycles and 230 mV after 30,000 voltage cycles at 1.2 $A/cm^2$. This compares with the baseline Sample 4, which fails due to a cross-over leak before 10,000 cycles and demonstrates both electrode and membrane ionomer degradation.

Figure 3:
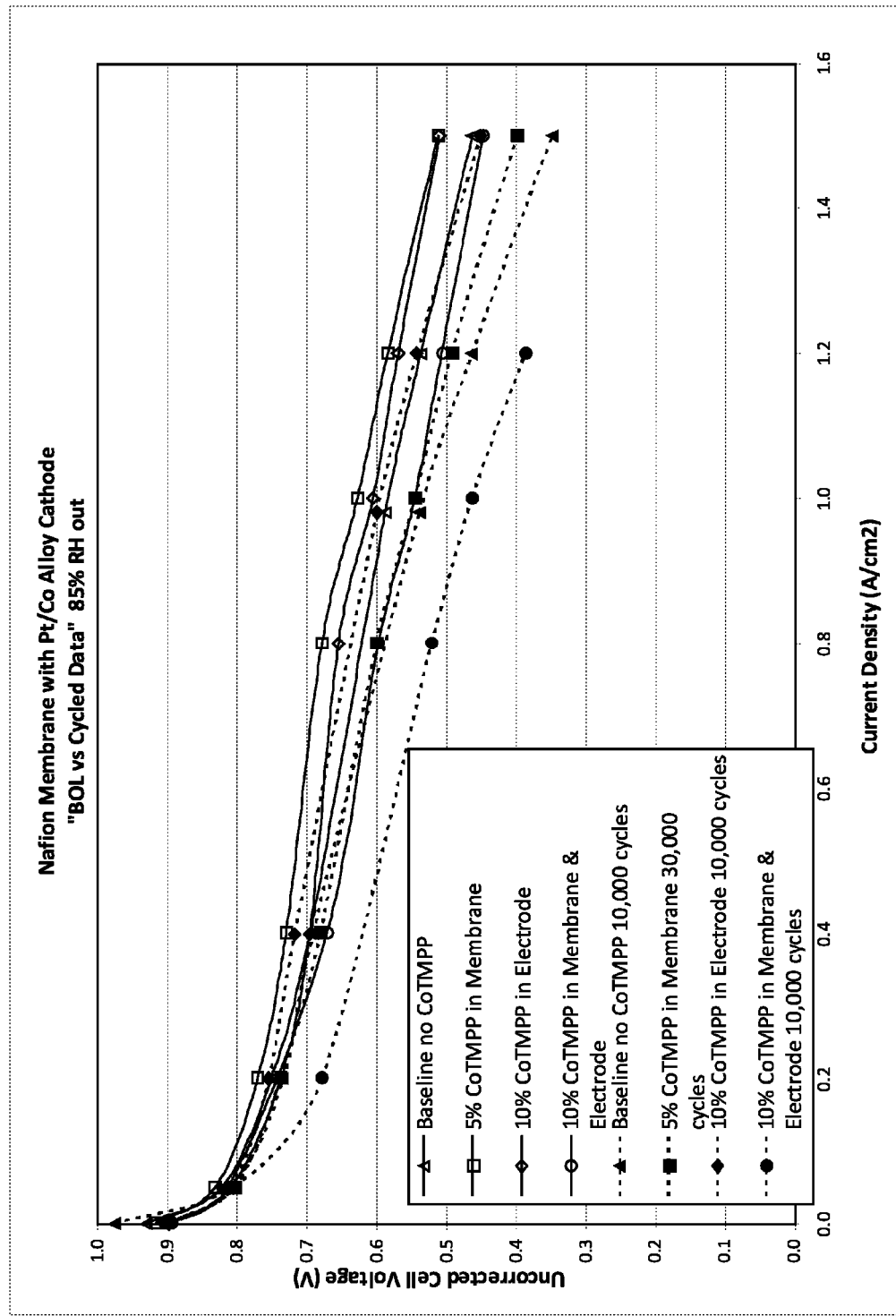
FIG. 3 is a plot of fuel cell performance (cell voltage versus current density, $A/cm^2$) at beginning of life and after cycling between 1 and 0.6 volts at 85% relative humidity exiting the cell for DE2020 Nafion® membranes and electrodes with and without cobalt(II) tetramethoxyphenylporphyrin (CoTMPP).

FIG. 3 is a plot of fuel cell performance (cell voltage versus current density, $A/cm^2$) at beginning of life and after cycling between 1 and 0.6 volts at 85% relative humidity exiting the cell for DE2020 Nafion® membranes and electrodes with and without cobalt(II) tetramethoxyphenylporphyrin (CoTMPP). For compositions see Table 1: Sample 1 (10% CoTMPP in membrane and in the electrode at beginning of life and after 10,000 [Sample 1a]); Sample 2 (10% CoTMPP in the electrode at beginning of life and after 10,000 [Sample 2a]; Sample 3 (5% CoTMPP in the membrane at beginning of life and after 30,000 cycles [Sample 3b]); and Sample 4 (baseline material with no CoTMPP at beginning of life). There is a voltage loss as a consequence of voltage cycling. For example, Sample 3 lost about 100 mV after 30,000 voltage cycles at 1.2 $A/cm^2$.

Figure 4:
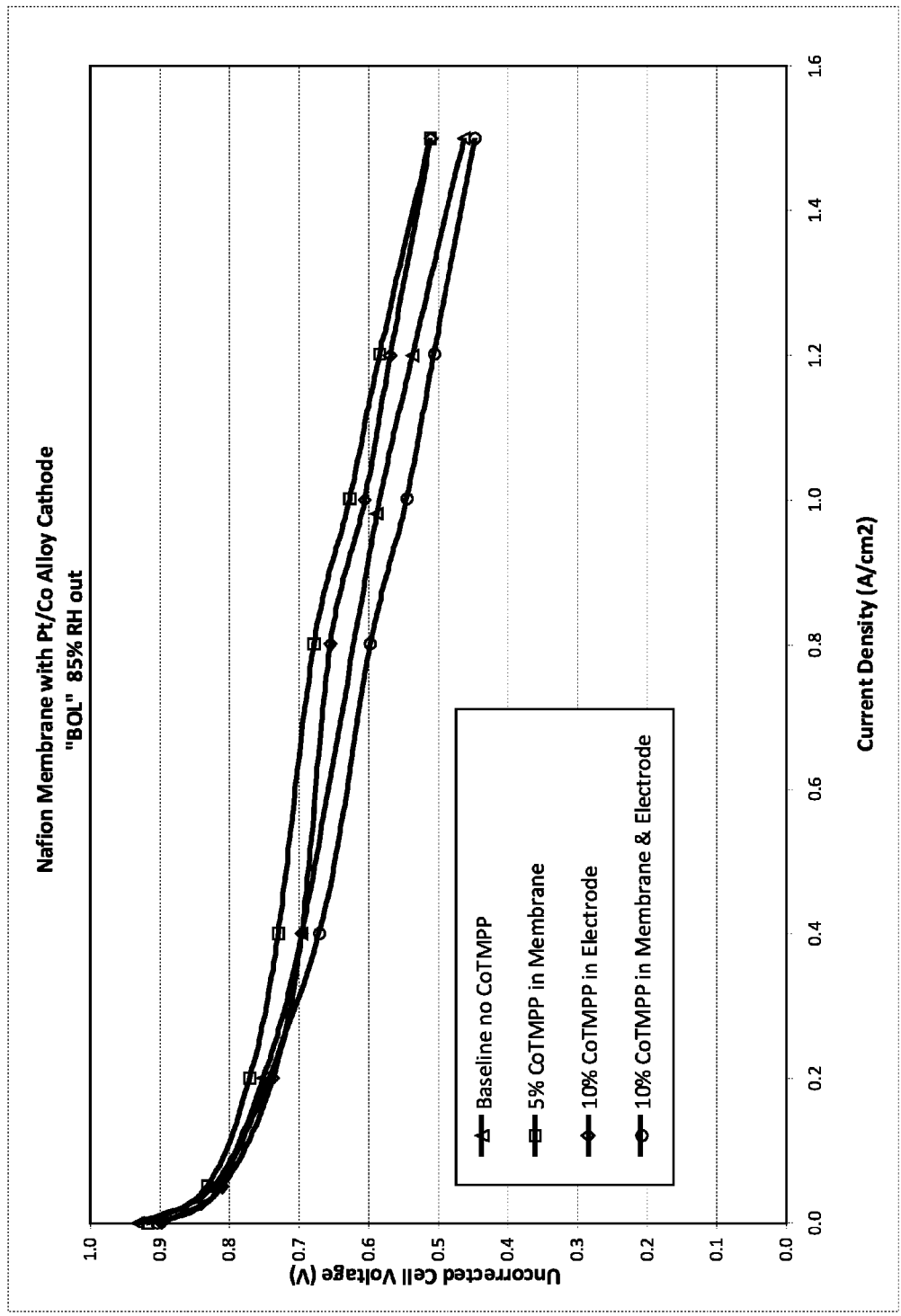
FIG. 4 is a plot of fuel cell performance (cell voltage versus current density, $A/cm^2$) at beginning of life at 85% relative humidity exiting the cell for DE2020 Nafion® membranes and electrodes with and without cobalt(II) tetramethoxyphenylporphyrin (CoTMPP).

FIG. 4 is a plot of fuel cell performance (cell voltage versus current density, $A/cm^2$) at beginning of life at 85% relative humidity exiting the cell for DE2020 Nafion® membranes and electrodes with and without cobalt(II) tetramethoxyphenylporphyrin (CoTMPP). For compositions see Table 1:

Sample 1 (10% CoTMPP in membrane and in the electrode); Sample 2 (10% CoTMPP in the electrode); Sample 3 (5% CoTMPP in the membrane); Sample 4 (baseline material with no CoTMPP). The addition of CoTMPP to electrodes or membranes has little or no impact on the beginning of life performance at 85% RHout.

Figure 5:
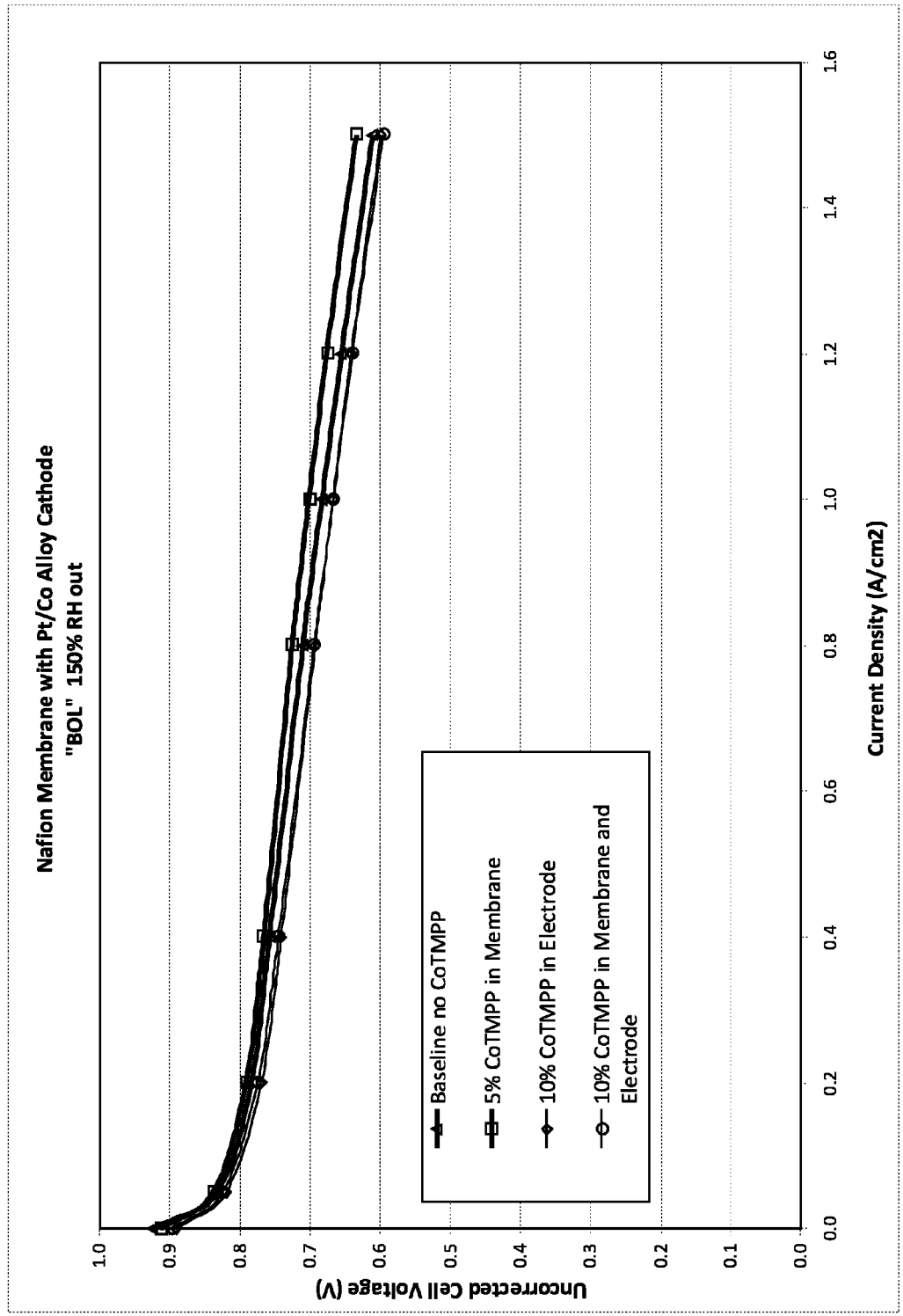
FIG. 5 is a plot of fuel cell performance (cell voltage versus current density, $A/cm^2$) at beginning of life at 150% relative humidity exiting the cell for DE2020 Nafion® membranes and electrodes with and without cobalt(II) tetramethoxyphenylporphyrin (CoTMPP).

FIG. 5 is a plot of fuel cell performance (cell voltage versus current density, A/cm$^2$) at beginning of life at 150% relative humidity exiting the cell for DE2020 Nafion® membranes and electrodes with and without cobalt(II) tetramethoxyphenylporphyrin (CoTMPP). For compositions see Table 1: Sample 1 (10% CoTMPP in membrane and in the electrode); Sample 2 (10% CoTMPP in the electrode); Sample 3 (5% CoTMPP in the membrane); Sample 4 (baseline material with no CoTMPP). The addition of CoTMPP to either or both electrodes and membrane has little or no impact on performance at 150% RHout.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A membrane/electrode assembly for fuel cell applications, the membrane/electrode assembly comprising:
    a cathode catalyst layer;
    an anode catalyst layer; and
    an ion conducting membrane positioned between the cathode catalyst layer and the anode catalyst layer, the ion conducting membrane comprising ion conducting polymer that comprises a perfluorocyclobutyl moiety; and a porphyrin-containing compound having formula 1:

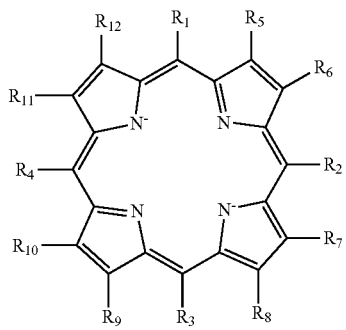

wherein:
    $R_1$, $R_2$, $R_3$, $R_4$ are each independently hydrogen, substituted or unsubstituted alkyl, aryl, substituted or unsubstituted phenyl, or phenylmethoxy;
    $R_5$, $R_6$, $R_7$, $R_8$, $R_9$, $R_{10}$, $R_{11}$, $R_{12}$ are each independently hydrogen, alkyl, or aryl, the ion conducting polymer that comprises a perfluorocyclobutyl moiety including polymer segments 3 and 4:

$$E_1(SO_2X)_d\text{—}P_1\text{-}Q_1\text{-}P_2 \qquad 3$$

$$E_2\text{-}P_3\text{-}Q_2\text{-}P_4 \qquad 4$$

connected by a linking group $L_1$ to form polymer units 5 and 6:

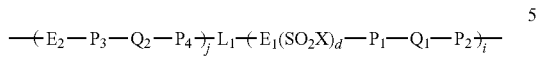

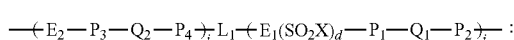

$Z_1$ is —SO$_2$X, —PO$_3$H$_2$, or —COX;
$E_1$ is an aromatic-containing moiety;
$E_2$ is an unsulfonated aromatic-containing and/or aliphatic-containing moiety;
$L_1$ is a linking group;
X is an —OH, a halogen, an ester, or

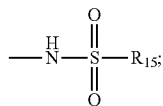

d is a number of $Z_1$ functional groups attached to $E_1$;
$P_1$, $P_2$, $P_3$, $P_4$ are each independently absent, —O—, —S—, —SO—SO$_2$—, —CO—, —NH—, NR$_{13}$—, —R$_{14}$—, and
$R_{13}$ is $C_{1\text{-}25}$ alkyl, $C_{1\text{-}25}$ aryl or $C_{1\text{-}25}$ arylene;
$R_{14}$ is $C_{1\text{-}25}$ alkylene, $C_{1\text{-}25}$ perfluoroalkylene, or $C_{1\text{-}25}$ arylene;
$R_{15}$ is trifluoromethyl, $C_{1\text{-}25}$ alkyl, $C_{1\text{-}25}$ perfluoroalkylene, $C_{1\text{-}25}$ aryl, or another $E_1$ group;
$Q_1$, $Q_2$ are each independently a fluorinated cyclobutyl moiety;
i is a number representing repetition of polymer segment 3; and,
j is a number representing repetition of a polymer segment 4.

2. The membrane/electrode assembly of claim 1 wherein $R_5$, $R_6$, $R_7$, $R_8$, $R_9$, $R_{10}$, $R_{11}$, $R_{12}$ are each hydrogen.

3. A membrane/electrode assembly for fuel cell applications, the membrane/electrode assembly comprising:
    a cathode catalyst layer;
    an anode catalyst layer; and
    an ion conducting membrane positioned between the cathode catalyst layer and the anode catalyst layer, the ion conducting membrane comprising ion conducting polymer that comprises a perfluorocyclobutyl moiety; and a porphyrin-containing compound having formula 1:

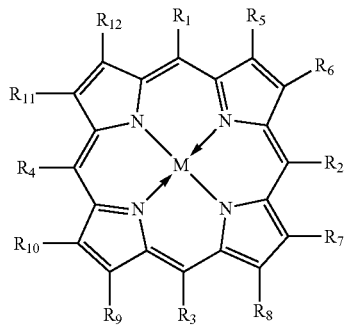

wherein $R_1, R_2, R_3, R_4, R_5, R_6, R_7, R_8, R_9, R_{10}, R_{11}, R_{12}$ are each independently hydrogen, alkyl, or aryl and M is a metal selected from the group consisting of $Co^{2+}, Co^{3+}, Fe^{2+}, Fe^{3+}, Mg^{1+}, Mg^{2+}, Mn^{1+}, Mn^{2+}, Mn^{3+}, ClMn^{3+}, HOMn^{3+}, Cu^{1+} Cu_{2+}, Ni^{1+}, Ni^{2+}, Pd^{1+}, Pd^{2+}R^{1+}, R^{2+}, R^{4+}, Vn^{4+}, Zn^{1+}, Zn^{2+}, Al^{3+}, B, Si(OH)_2^{2+}, Al^{3+}, HOIn^{3+}, HOIn^{3+}, Pb^{2+}, Ag^{30}, Sn^{2+}, Sn^{4+}, Ti^{3+}, Ti^{4+}, VO^+, Pt^{2+}, Ce^{3+}$, and $Ce^{4+}$ and wherein the ion conducting polymer that comprises a perfluorocyclobutyl moiety includes polymer segments 3 and 4:

$$E_1(SO_2X)_d\text{—}P_1\text{-}Q_1P_2 \quad \quad 3$$

$$E_2\text{-}P_3\text{-}Q_2\text{-}P_4 \quad \quad 4$$

connected by a linking group $L_1$ to form polymer units 5 and 6:

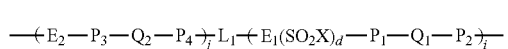
5

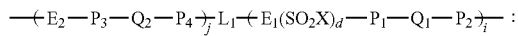
6

$Z_1$ —$SO_2X$, —$PO_3H_2$, or —COX;
$E_1$ is an aromatic-containing moiety;
$E_2$ is an unsulfonated aromatic-containing and/or aliphatic-containing moiety;

$L_1$ is a linking group;
X is an —OH, a halogen, an ester, or

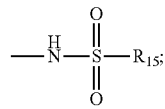

d is a number of $Z_1$ functional groups attached to $E_1$;
$P_1, P_2, P_3, P_4$ are each independently absent, —O—, —S—SO—$SO_2$—, —CO—, —NH—, —$NR_{13}$—, —$R_{14}$—, and
$R_{13}$ is $C_{1-25}$ alkyl, $C_{1-25}$ aryl or $C_{1-25}$ arylene;
$R_{14}$ is $C_{1-25}$ alkylene, $C_{1-25}$ perfluoroalkylene, or $C_{1-25}$ arylene;
$R_{15}$ is trifluoromethyl, $C_{1-25}$ alkyl, $C_{1-25}$ perfluoroalkylene, $C_{1-25}$ aryl, or another $E_1$ group;
$Q_1, Q_2$ are each independently a fluorinated cyclobutyl moiety;
i is a number representing repetition of polymer segment 3; and,
j is a number representing repetition of a polymer segment 4.

4. The membrane/electrode assembly of claim 3 wherein the porphyrin-containing compound is Co(II)tetramethoxyphenylporphyrin.

* * * * *